United States Patent [19]

Tamborski et al.

[11] 4,454,349

[45] Jun. 12, 1984

[54] PERFLUOROALKYLETHER SUBSTITUTED PHENYL PHOSPHINES

[75] Inventors: Christ Tamborski, Dayton; Carl E. Snyder, Jr., Trotwood; John B. Christian, Yellow Springs, all of Ohio

[73] Assignee: The United States of America as represented by the Secretary of the Air Force, Washington, D.C.

[21] Appl. No.: 418,115

[22] Filed: Sep. 14, 1982

[51] Int. Cl.³ .............................. C07F 9/52; C07F 9/50
[52] U.S. Cl. ........................................... 568/13; 568/8; 568/16; 568/17
[58] Field of Search .......................... 568/8, 13, 16, 17

[56] References Cited

U.S. PATENT DOCUMENTS

| | | | |
|---|---|---|---|
| 3,393,151 | 7/1968 | Dolle, Jr. et al. | 252/49.9 |
| 3,396,197 | 8/1968 | Sharts | 260/606.5 |
| 3,481,872 | 12/1969 | Dolle, Jr. et al. | 252/49.9 |
| 3,481,988 | 12/1969 | Wunsch et al. | 260/606.5 |
| 3,483,129 | 12/1969 | Dolle, Jr. et al. | 252/49.9 |
| 3,499,041 | 3/1970 | Tamborski | 260/612 |
| 3,567,802 | 3/1971 | Garth | 260/950 |
| 4,011,267 | 3/1977 | Tamborski et al. | 260/606.5 P |
| 4,043,926 | 8/1977 | Snyder et al. | 252/49.9 |

OTHER PUBLICATIONS

Chemical Abstracts 94: 49852j (1981).
Chemical Abstracts 92: 164038u (1980).
Chemical Abstracts 88: 9569s (1978).
Chemical Abstracts 93: 132553n (1980).

*Primary Examiner*—Helen M. S. Sneed
*Attorney, Agent, or Firm*—Donald Singer; Charles E. Bricker

[57] ABSTRACT

Fluorinated phosphines having the general formula

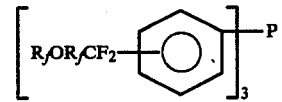

wherein $R_fOR_f$— is a perfluoroalkylether group containing at least one ether linkage are useful as antioxidation additives for perfluorinated fluids.

7 Claims, No Drawings

PERFLUOROALKYLETHER SUBSTITUTED PHENYL PHOSPHINES

RIGHTS OF THE GOVERNMENT

The invention described herein may be manufactured and used by or for the Government of the United States for all governmental purposes without the payment of any royalty.

BACKGROUND OF THE INVENTION

This invention relates to perfluoroalkylether substituted aryl phosphines.

Because of their thermal stability, perfluorinated fluids have a great potential for use as engine oils, hydraulic fluids and greases. However, a serious drawback in their use results from the fact that certain metals are corroded by such fluids at temperatures of about 550° F. and above in an oxidative environment.

In U.S. Pat. No. 3,393,151, issued to one of us as a coinventor on July 16, 1968, lubricants are disclosed that comprise a perfluorophenyl phosphorus compound. In U.S. Pat. No. 3,499,041 issued to one of us on Mar. 3, 1970, certain perfluoroarylphosphines are disclosed as being corrosion and oxidation inhibitors in polyfluoroalkylether polymeric fluids, while the phosphorus compounds described in these patents exhibit protective properties, they are only poorly soluble in perfluorinated fluids at low temperatures. Also, certain members of the classes of phosphorus compounds possess high volatility characteristics for long-term high-temperature applications. Because of these limitations, perfluorinated fluids containing such additives are not completely satisfactory for use in long-term, wide-temperature range (−100° F. to >550° F.) application.

In U.S. Pat. No. 4,011,267 issued to two of us as coinventors on Mar. 8, 1977, certain perfluoroalkylether-substituted aryl phosphines are disclosed which have the following formula

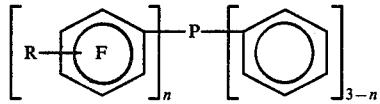

where R is a perfluoroalkylether group and n is 1, 2 or 3. Incorporation of these compounds in perfluoroalkylether fluids, e.g., fluids of the type disclosed in U.S. Pat. No. 3,393,151, inhibits the oxidation-corrosion of various metals with which the fluids come into contact. These additives also prevent decomposition of such fluids when exposed to a high-temperature oxidative environment. These additives exhibit better low-temperature solubility and lower volatility than the earlier known perfluoroarylphosphines. These compounds are, however, relatively expensive, thereby limiting their widespread usage. What is desired are compounds having the desirable characteristics of the compounds disclosed in U.S. Pat. No. 4,011,267, at a relatively lower cost.

It is an object of this invention to provide improved antioxidation-anti-corrosion additives for perfluorinated fluids.

Other objects and advantages of the invention will become apparent to those skilled in the art upon consideration of the accompanying disclosure.

DESCRIPTION OF THE INVENTION

The present invention resides in perfluoroalkylether-substituted aryl phosphines having the general formula

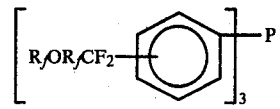

wherein $R_fOR_f$ is a perfluoroalkylether group containing at least one ether linkage. Examples of perfluoroalkylether groups include the following
$C_3F_7O[CF(CF_3)CF_2O]_xCF(CF_3)-$,
$C_2F_5O(CF_2CF_2O)_yCF_2-$, and
$CF_3O(CF_2O)_zCF_2-$,
where x, y and z are zero or an integer having a value of 1 to 20, preferably 1–4, inclusive.

The perfluoroalkylether-substituted aryl phosphines can be prepared according to the procedure represented by the following equations:

(A)

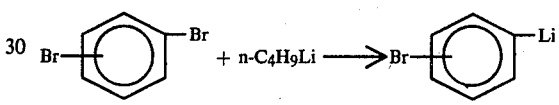

(B)

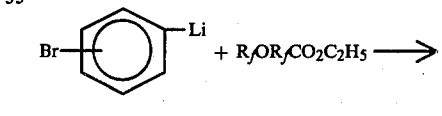

(C)

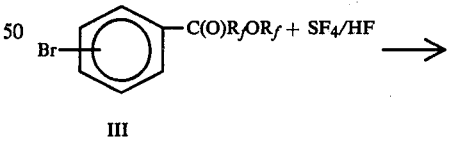

(D)

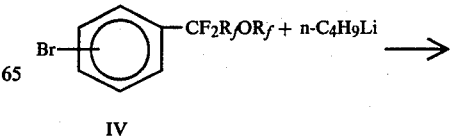

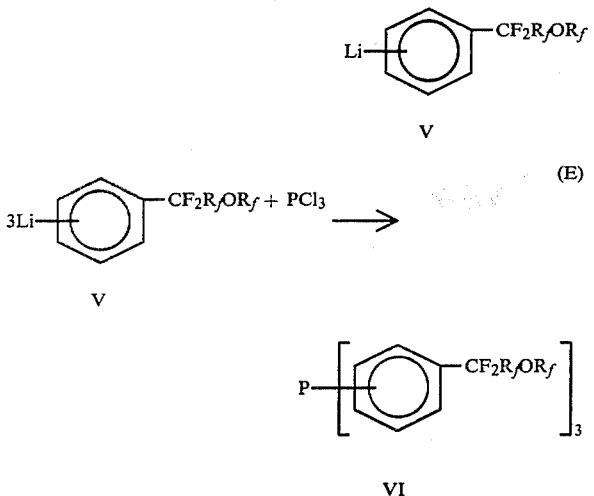

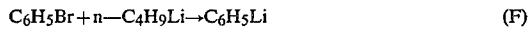
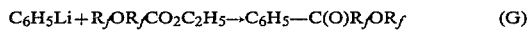
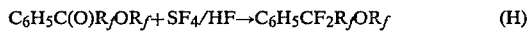

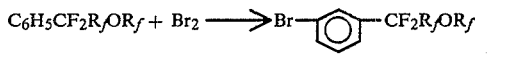

As seen from reaction (A), dibromobenzene is reacted with n-butyllithium. The dibromobenzene can be 1,2—, 1,3—, or 1,4—. The reaction is carried out at a low temperature, e.g., −70° to −80° C., in a suitable solvent or mixture of solvents, for a time sufficient to form compound I, e.g., 15 minutes to 2 hours.

As seen from reaction (B), the compound I is reacted with a perfluoroalkylether ester (II) to form a ketone (III). A variety of esters (II) can be used in this step which in turn will provide a variety of ketones (III) depending on the group $R_fOR_f$—. The reaction (B) is carried out at a low temperature, e.g., −70° to −80° C., by adding the ester II slowly to the organolithium intermediate I. The compounds I and II are allowed to react for a suitable period, e.g., ½ to 12 hours, after which the reaction mixture is hydrolyzed. The solvent layer is phase separated and dried. The ketone III is then recovered by fractional distillation.

As shown by equation (C), the ketone III is fluorinated by reacting the same with sulfur tetrafluoride in the presence of HF. The reaction is carried out by adding anhydrous hydrogen fluoride and sulfur tetrafluoride to a cooled pressure vessel containing the ketone. The vessel is sealed, then rocked and maintained at a temperature ranging from about 150° to 200° C. for a period of about 12 to 24 hours. This reaction may be carried out in a suitable liquid medium. After cooling, the vessel is vented. If the liquid medium is a solvent for the fluorinated product IV, any solids present in the reaction mixture are removed by filtration. Otherwise, the contents of the vessel are washed with a solvent and solids are removed by filtration. The solvent is evaporated and the residue is fractionally distilled to yield the fluorinated product IV.

The fluorinated product IV is then reacted with n-butyllithium, as shown by reaction (D). The reaction is carried out by mixing solutions of the compounds under conditions to form the intermediate V, e.g., about −70° to −80° C. for about 15 minutes to 1 hour. At the end of the reaction period, a solution of phosphorous trichloride is added to compound V, and the reaction occurs to yield a phosphine compound VI of this invention. In the reaction shown by equation (E), the reaction mixture is stirred for about 0.5 to 2 hours, allowing the mixture to warm slowly to about 0° C., after which the reaction mixture is allowed to warm slowly to room temperature. Then reaction mixture is hydrolyzed, then phase separated. The bottom viscous layer is washed with water, diluted with a suitable solvent, e.g., a fluorinated solvent, such as hexafluorobenzene or trifluorotrichloroethane, and then dried. After filtration and removal of the solvent, the phosphine product VI is obtained by fractional distillation or column chromatography in the form of a viscous liquid.

Alternatively, the tris(3-perfluoroalkylether phenyl)phosphine can be prepared by the procedure represented, in part, by the following equations:

$$C_6H_5Br + n\text{-}C_4H_9Li \rightarrow C_6H_5Li \tag{F}$$

$$C_6H_5Li + R_fOR_fCO_2C_2H_5 \rightarrow C_6H_5\text{—}C(O)R_fOR_f \tag{G}$$

$$C_6H_5C(O)R_fOR_f + SF_4/HF \rightarrow C_6H_5CF_2R_fOR_f \tag{H}$$

(I)

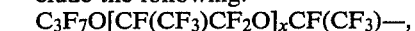
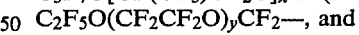

It will be appreciated by those skilled in the art that the reactions represented by equations (F), (G) and (H) are essentially the same as those represented by equations (A), (B) and (C), respectively. The perfluoroalkylether benzene compound VII is brominated in the meta position, as shown by the equation (I). In this reaction, bromine is added to compound VII dissolved in trifluoroacetic acid, in the presence of a reaction promoting amount of silver trifluoroacetate, under reflux conditions. After the bromine is completely added and analysis indicates complete conversion of the compound VII to the compound IV', the reaction is cooled, hydrolyzed with dilute HCl and filtered. The compound IV' is obtained by fractional distillation.

Conversion of the meta-derivative IV' to the phosphine VI is accomplished according to the reactions shown in equations (D) and (E), described previously.

Any fluoroester can be used that corresponds to the formula $R_fOR_fCO_2R$, where $R_fOR_f$ represents a perfluoroalkylether group containing at least one ether linkage, and R is a lower alkyl group, generally methyl or ethyl. Examples of perfluoroalkylether groups include the following:
$C_3F_7O[CF(CF_3)CF_2O]_xCF(CF_3)$—,
$C_2F_5O(CF_2CF_2O)_yCF_2$—, and
$CF_3O(CF_2O)_zCF_2$—,
where x, y and z are zero or an integer having a value of 1 to 20, preferably 1–4. The esters $R_fOR_fCO_2R$ can be prepared from the corresponding acyl halides $R_fOR_fC(O)X$, where X is a halogen, as disclosed in U.S. Pat. Nos. 3,124,599; 3,214,478 and 3,721,696. Thus, depending upon the ester employed, a variety of ketones can be synthesized according to equations (B) and (G).

The fluorinated phosphines compounds of this invention are useful as additives for hydraulic fluids and greases prepared from perfluoroalkylether base fluids, e.g., fluids of the type disclosed in U.S. Pat. No. 3,393,151. The compounds of this invention prevent the decomposition of such fluids when exposed to a high temperature (500°–650° F.) oxidative environment. Of primary importance, the compounds of this invention exhibit low-temperature solubility and low volatility in such fluids. In general, only small amounts of these additives are required, e.g., about 0.05 to 5.0 percent by weight of the base fluid.

The following examples illustrate the invention.

EXAMPLE I

Synthesis of 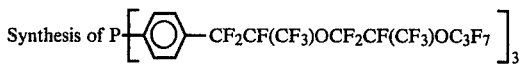

To a solution of 49.5 g (0.21 mole) of 1,4-dibromobenzene in 500 ml of diethyl ether at −78° C. was added 86.6 ml of n-butyllithium (2.42 M in n-hexane, 0.21 mole) over a period of about 2 hours. During the addition, the originally colorless solution turned a cloudy pale yellow and the reaction temperature rose to −73° C. The reaction mixture was cooled to −78° C., then 11 g (0.21 mole) of $C_3F_7OCF(CF_3)CF_2OCF(CF_3)CO_2C_2H_5$ was added over a period of one hour. A pale yellow solution was obtained. During the addition, reaction temperature rose to −75° C. This reaction mixture was stirred for about 1 hour at −78° C., then hydrolyzed with 500 ml 2N HCl.

The hydrolyzed mixture was allowed to warm to room temperature then phase separated. The aqueous layer was extracted three times with 100 ml portions of diethyl ether. The combined organic layers were dried over anhydrous magnesium sulfate. The diethyl ether and any low boiling liquids were than removed with a rotary evaporator at about 40° C. The crude product was distilled to give the pure ketone (structure III), b.p. 91° C./1.1 mm in 83% yield. NMR and IR analyses were consistent with the proposed structure.

56 g (0.087 mole) of the ketone were placed in a 300 ml Monel pressure vessel. The vessel was cooled in a dry ice-acetone bath, then about 25 ml anhydrous hydrogen fluoride, about 34 g sulfur tetrafluoride and 100 ml Freon 113 were added to the vessel. The pressure vessel was sealed, rocked and heated to 180° C. for 18 hours. The vessel was cooled, vented, and the contents were stored over about 25 g of KF. The liquid was separated from the solids, and the solvent evaporated. The residue was fractionally distilled to yield the fluorinated product (structure IV), b.p. 100° C./2 mm, in 80% yield. NMR, IR, elemental, and mass spectral analyses were consistent with the proposed structure.

To a solution of 33.1 g (0.050 mole) of the fluorinated product (IV) in 100 ml diethyl ether at 0° C. was slowly added 20 ml of a 2.5 M hexane solution (0.05 mole) of n-butyllithium. After one hour a solution of 2.1 g (0.015 mole) of phosphorous trichloride in diethyl ether was slowly added. This reaction mixture was stirred at 0° C. for 1 hour, then allowed to warm slowly to room temperature. The reaction mixture was hydrolyzed with dilute HCl, phase separated and the viscous bottom layer was washed repeatedly with water. Distillation at reduced pressure yielded the desired product, b.p. 200° C./0.1 mm, in 86% yield. NMR and IR analyses were consistent with the desired product. Elemental analysis of the product gave the following results: Calc'd for $P(C_{15}H_4F_{19}O_2)_3$: C, 30.30; H, 0.68. Found: C, 30.62; H, 0.76.

EXAMPLE II

Synthesis of 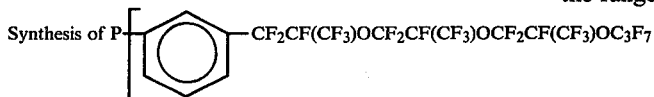

Into a 3-neck reaction flask was placed 110 g (0.148 mole) of $C_6H_5CF_2CF(CF_3)[OCF_2CF(CF_3)]_2OC_3F_7$, 39.2 g (0.178 mole) of $CF_3CO_2Ag$ and 200 ml of $CF_3COOH$. The contents were heated to reflux, then 28.4 g (0.178 mole) of bromine was added slowly through a dropping funnel. A precipitate formed immediately. Periodic aliquots were taken and analyzed by gas chromatography. When the analysis indicated maximum consumption of the starting material, the reaction was stopped, cooled and hydrolyzed with dilute HCl. The precipitate was filtered and the filtrate was extracted with diethyl-ether. The ether extracts were dried and the solvent was then removed on a rotary evaporator leaving the crude product. Fractional distillation provided the desired m-bromo-drivative (structure IV') b.p. 94° C./0.09 mm in 90% yield. NMR, IR and mass spectral analyses were consistent with the proposed structure.

To a solution of 20.6 g (0.025 mole) of the meta-bromoperfluoroalkylether benzene compound in 100 ml of diethyl ether, cooled to 0° C., was added slowly 11 ml of a 2.2 M n-hexane solution ( 0.0242 mole) of n-butyllithium. After one hour a solution of 1.05 g (0.0077 mole) of phosphorus trichloride in diethyl ether was slowly added. This reaction mixture was stirred at 0° C. for 1 hour, then allowed to warm to room temperature. The reaction mixture was hydrolyzed with dilute HCl, phase separated, and the viscous bottom layer was washed repeatedly with water. The crude product was placed on a silica gel column and eluted using a petroleum ether (boiling range (30°-60° C.). 15.5 g of the desired product, representing about 90% yield, was obtained. NMR and IR analyses were consistent with the desired structure.

Elemental Analysis Calc'd for $PC_{54}H_{12}F_{75}O_9$: C, 28.69; H, 0.54. Found: C, 28.00; H, 0.42.

It will be evident to those skilled in the art that modifications of the present invention can be made without departing from the spirit and scope of the invention.

We claim:

1. A perfluoroalkylether-substituted aryl phosphine of the gfeneral formula

wherein $R_fOR_f$— is a perfluoroalkylether group containing at least one ether linkage.

2. The compound of claim 1 wherein said $R_fOR_f$— is $C_3F_7O[CF(CF_3)CF_2O]_xCF(CF_3)$—, and wherein x has a value ranging from 0 to 20.

3. The compound of claim 2 wherein x has a value in the range of 1 to 4.

4. The compound of claim 1 wherein said $R_fOR_f$— is $C_2F_5O(CF_2CF_2O)_yCF_2$— wherein y has a value in the range of 0 to 20.

5. The compound of claim 4 wherein y has a value in the range of 1 to 4.

6. The compound of claim 1 wherein said $R_fOR_f$— is $CF_3O(CF_2O)_zCF_2$— wherein z has a value in the range of 0 to 20.

7. The compound of claim 6 wherein z has a value in the range of 1 to 4.

* * * * *